United States Patent [19]

Landis

[11] Patent Number: 4,864,653

[45] Date of Patent: Sep. 12, 1989

[54] PROTECTIVE SHIELD AND VISOR SUPPORTING SAME

[76] Inventor: Timothy J. Landis, 2006 McLaren Ave., Roseville, Calif. 95661-4945

[21] Appl. No.: 194,150

[22] Filed: May 16, 1988

[51] Int. Cl.$^4$ .............................................. A61F 9/00
[52] U.S. Cl. ........................................................... 2/9
[58] Field of Search .................. 2/9, 10, 11, 12, 13, 2/DIG. 11

[56] References Cited

U.S. PATENT DOCUMENTS

| | | | |
|---|---|---|---|
| D. 228,700 | 10/1973 | Gager | 2/10 X |
| 797,293 | 8/1905 | Lang | 2/12 |
| 1,279,884 | 9/1918 | Le Roche | |
| 1,582,164 | 4/1926 | Burstyn | |
| 1,763,899 | 6/1930 | McClay et al. | 2/12 |
| 2,179,719 | 11/1939 | Goskey | 2/10 |
| 2,262,449 | 0/1941 | Bregeleisen | 2/9 |
| 2,598,265 | 5/1952 | Jones | 2/427 |
| 2,614,255 | 10/1952 | Ellis | 2/12 |
| 2,638,593 | 5/1953 | Eloranta | 2/12 |
| 2,665,686 | 1/1954 | Wood | 2/9 |
| 2,774,970 | 12/1956 | Du Bois | |
| 2,798,222 | 7/1957 | Evans | 2/9 |
| 2,818,859 | 1/1958 | Peterson | 2/9 |
| 2,978,709 | 4/1961 | Atlia | |
| 3,049,716 | 8/1962 | Stegeman | 2/12 X |
| 3,103,667 | 9/1963 | Rogowski | |
| 3,152,588 | 10/1964 | Rogowski | 2/9 |
| 3,298,031 | 1/1967 | Morgan | |
| 3,346,875 | 10/1967 | Weisberger | |
| 3,475,766 | 11/1969 | Raschke | 2/9 |
| 3,678,929 | 7/1972 | Buscher | |
| 4,250,577 | 2/1979 | Smith | |
| 4,475,254 | 6/1984 | Bay | 2/12 |
| 4,701,965 | 10/1987 | Landis | 2/9 X |
| 4,768,231 | 9/1988 | Schrack | 2/13 X |

FOREIGN PATENT DOCUMENTS

| | | |
|---|---|---|
| 519567 | 2/1931 | Fed. Rep. of Germany . |
| 688227 | 1/1940 | Fed. Rep. of Germany .............. 2/9 |
| 480364 | 7/1915 | France . |
| 1477618 | 4/1967 | France . |
| 1527271 | 4/1968 | France . |
| 317863 | 1/1957 | Switzerland . |
| 513750 | 10/1939 | United Kingdom ...................... 2/9 |

OTHER PUBLICATIONS

Gershman, Maurice, "Self Adhering Nylon Tapes", *The Journal of the AMA.*, vol. 168, No. 7, p. 930, date Oct. 1958.

*Primary Examiner*—Werner H. Schroeder
*Assistant Examiner*—Jeanette E. Chapman
*Attorney, Agent, or Firm*—Julian Caplan

[57] ABSTRACT

A mask to protect physicians, dentists and technicians from spatter from patients afflicted with various diseases (including A.I.D.S.) is assembled from two parts, which may be shipped and stored flat, may be sterilized, and are so inexpensive in materials and cost of fabrication that they may be disposed of after use. In one form of the invention, a visor is formed of a flat piece of sheet rubber having two tails provided with interfitting snaps. The tails are brought around the back of the head and the proper snaps or other fasteners adjusted to accommodate the head size of the wearer. This operation causes the flat sheet to assume a curved visor shape fitting around the forehead. In another embodiment, a hole is punched in a curved sheet of elastic material of a size so that it may be drawn down over the head. In a further embodiment, a piece of stretchable rubber-like tubing has opposite ends attached to ends of the tails of the visor. The tubing is stretched around the back of the head, causing the visor to assume an upward convex shape and causing its inner edge to engage the forehead of the wearer. The shape of the sheet provides a bill similar to the preceding modification. Slits are formed near the outer edge of the visor. A transparent shield has dovetail projections on its upper edge which snap through the slits. Other cooperating fastening means may be used to assemble the visor and shield. The shield is supported by the visor and hangs down to about the chin, protecting the eyes, nose and mouth.

9 Claims, 3 Drawing Sheets

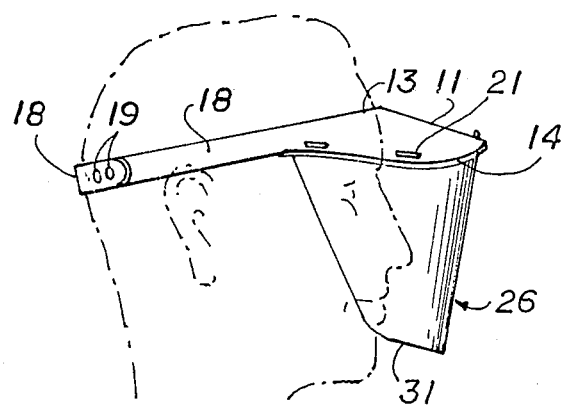
Fig.1
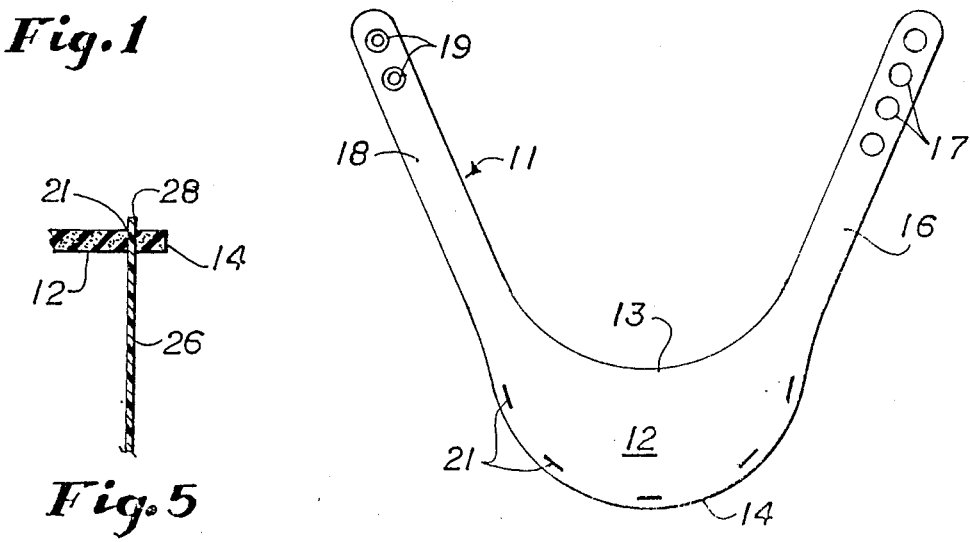
Fig.5
Fig.2
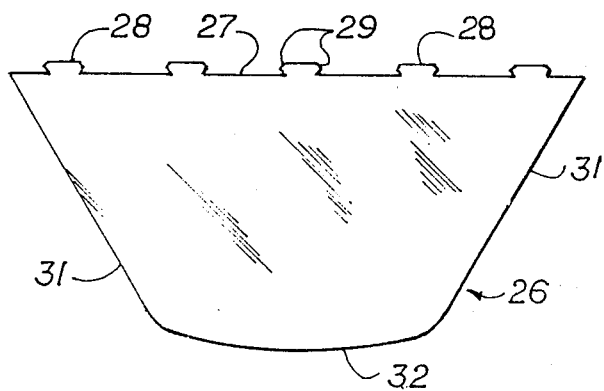
Fig.3
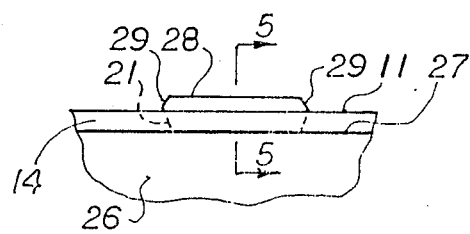
Fig.4

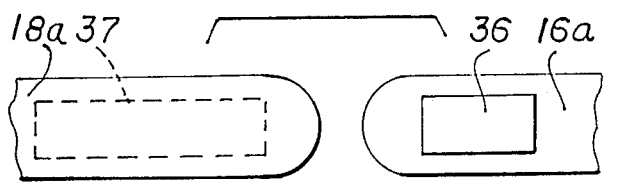
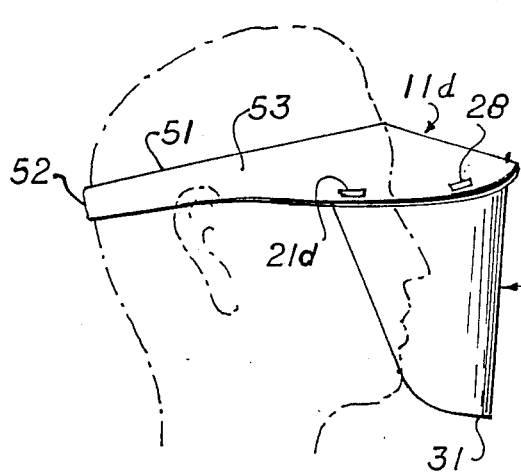
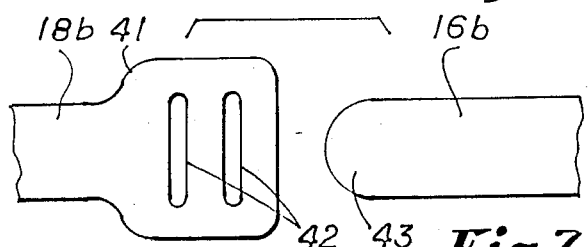
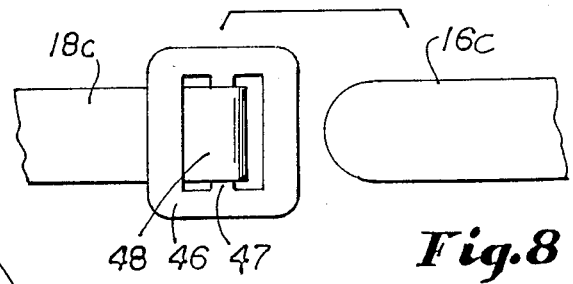
Fig.6
Fig.7
Fig.8
Fig.9
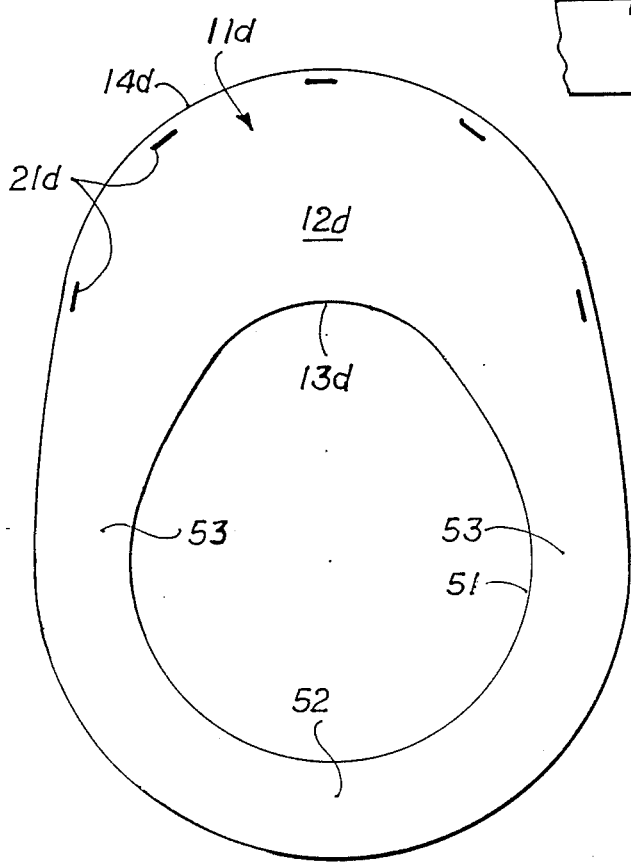
Fig.10
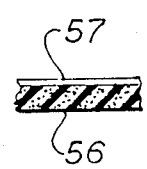
Fig.11

PROTECTIVE SHIELD AND VISOR SUPPORTING SAME

CROSS-REFERENCE TO RELATED APPLICATIONS

Reference is made to Applicant's U.S. Pat. No. 4,701,965 on which the present invention is an improvement in the sense that it may be used for medical uses as well as in dentistry and may be of inexpensive construction and thus disposable.

BACKGROUND OF THE INVENTION

1. Field of the Invention

This invention relates to a new and improved mask for use by surgeons, dentists and others to avoid contamination with germs and viruses of their patients and customers. A visor, which is adjustable to fit the head size of the wearer, supports a transparent plastic shield of sheet plastic which attaches to the visor and extends down to below the level of the mouth of the wearer and around the sides of the head, thus providing superior frontal and lateral protection from splashing and spattering with bodily fluids.

2. Description of Related Art

Surgical masks of gauze and paper have been used to prevent intercontamination of doctor and patient. However, wearing such masks is hot and uncomfortable and, frequently, frightening to patients. Putting the masks on and removing them are time-consuming and sometimes difficult. Breath condenses within the mask and hence the latter becomes saturated with moisture and thereby fails to be an effective barrier to viruses and bacteria.

Surgical masks cause the wearer to re-inhale exhaled breath causing the $CO_2$ content of the blood to rise. The result of this may be increased heart and respiration rates and higher body temperatures and perspiration.

U.S. Pat. No. 4,701,965 illustrates a visor-type mask dentists and dental technicians which is commercially successful. This reference shows a visor which attaches the head and a transparent shield supported thereby. The present invention differs in a number of respects. A primary difference is that in one embodiment of the present invention the visor is initially flat and foldable and has a pair of tails which extend around the back of the head and means on the ends of the tails so that the visor is adjustable for different head sizes. In a second embodiment a hole is stamped in a sheet of stretchable material so that as the visor is pulled down, the top of the head projects through the hole and the margin of the hole extends across the forehead, around both sides and the back. In still another embodiment the "tails" of the first embodiment are truncated; the ends of a flexible tube are adjustably attached to the visor by threading the ends through holes in the tails; the tube is drawn back behind the user's head.

The attachment of the transparent shield to the visor likewise is simplified as hereinafter appears.

The present invention is particularly suited to surgical use in that it may be sterilized (as by ethylene dioxide gas) before and between uses and may be discarded after a single use.

Surgeons find use of the device very comfortable even during prolonged operations since localized pressure on the head does not occur and, further, the device is lightweight.

Other references are discussed in U.S. Pat. No. 4,701,965 and additional references were cited as references by the U.S. Patent and Trademark Office prior to the issuance of said patent.

SUMMARY OF THE INVENTION

The present invention consists of two main pieces. A visor of a sheet of rubber or rubber-like material is initially flat and foldable. In one form of the invention, the visor consists of a central peaked bill and tails which extend beyond the central portion of the visor and are provided with spaced male and female snaps so that the tails may be brought around the back of the head and snapped together in such a way as to adjust to the head size of the wearer. Alternatively the ends of the tails may be adjustably fastened by buckles, adhesive strips, Velcro-type fasteners, and other suitable devices. Slits may be formed along the outer margin of the central portion.

In another preferred embodiment the visor may be formed of a stretchable material with a hole slightly smaller than the head and drawn down over the head. Thus the use of fasteners for the tails is eliminated.

In still another embodiment a stretchable rubber-like tube passes behind the head of the wearer. The ends of the tube are fitted through holes in the truncated ends of the tails of the visor.

When the visor is adjusted on the head the visor fits around the forehead and extends downward-forward away from the head in a peaked bill. Contact with the head is substantially continuous all around. Contaminants are not likely to fall inside the shield by passage through a gap between the visor and the head of the user.

A removable, transparent, flexible plastic shield is suspended from the front edge of the visor. In a preferred form, the visor has dovetail projections along its upper edge which slip into the slits in the visor and lock therein. Alternatively the shield may be attached to the visor by snap, adhesive, Velcro materials or other means. The shield curves outwardly and extends downward so as to protect the eyes, nose and mouth of the wearer from contamination from the front or sides.

Further, the shield apertured and projections on the forward edge of the visor may fit through the apertures.

When the shield is in place it is supported by the visor and protects the eyes, nose and mouth from contamination by blood, body fluids and the like, of the patient. Because the shield is forward of the mouth and nose, air may flow up from below the face and from the sides, so that carbon dioxide buildup from re-breathing expelled air, fogging of the eyeglass lenses of the wearer, and saturation of the mask by splattering or splashing with bodily fluids do not occur.

The visor and shield are inexpensively fabricated by stamping from flat sheets of material, thus avoiding more expensive techniques such as injection molding and various fabricating techniques.

Because the visor is of a resilient material, it is comfortable to wear, a feature which is particularly important when the mask is worn during surgical procedures which are lengthy.

Other objects of the present invention will become apparent upon reading the following specification and referring to the accompanying drawings in which similar characters of reference represent corresponding parts in each of the several views.

IN THE DRAWINGS:

FIG. 1 is a profile view of one form of the invention in wearing position.

FIG. 2 is a plan view of a visor.

FIG. 3 is a plan view of a shield.

FIG. 4 is an enlarged fragmentary view of a portion of a shield.

FIG. 5 is a sectional view taken substantially along line 5—5 of FIG. 4.

FIGS. 6, 7 and 8 are fragmentary views of alternate ways of connecting the straps of FIG. 2.

FIG. 9 is a view similar to FIG. 1 of a modification.

FIG. 10 is a view similar to FIG. 2 of the modification of FIG. 9.

FIG. 10 is an enlarged sectional view of a portion of a visor in accordance with FIG. 9.

DESCRIPTION OF PREFERRED EMBODIMENTS

Figure 12:
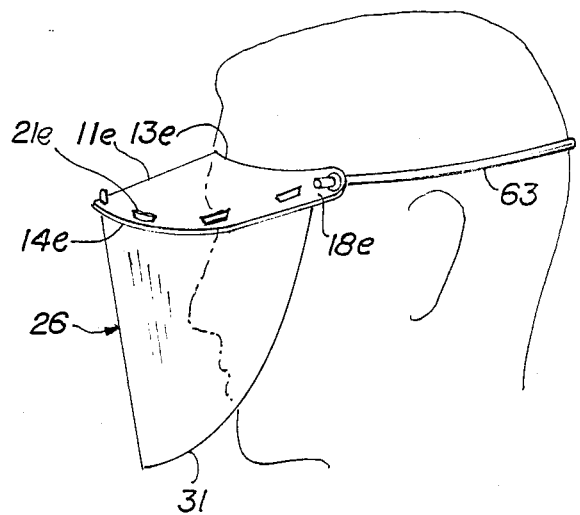
FIG. 12 is a view similar to FIG. 1 of another modification of the invention.
Figure 13:
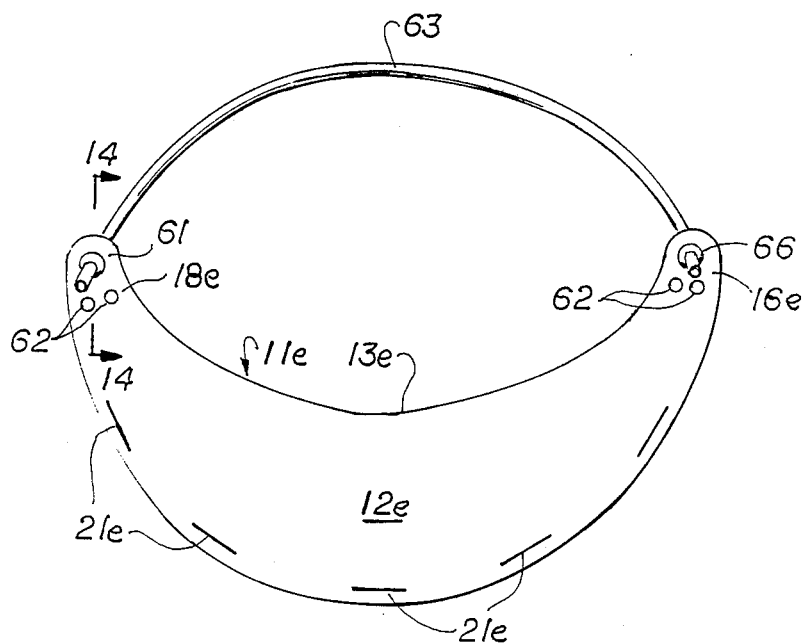
FIG. 13 is an enlarged perspective view of the modification of FIG. 12.
Figure 14:
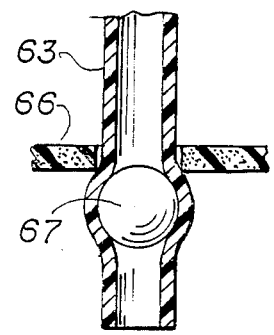
FIG. 14 is a further enlarged, fragmentary sectional view taken substantially along line 14—14 of FIG. 13.

As shown in FIGS. 1—5, in one embodiment, visor 11 is preferably formed of a sheet of cross-linked polyethylene, rubber or rubber-like material about 3/32 inches in thickness. Other materials and other thicknesses are contemplated. The visor may be made in various colors. As shown in FIG. 11, one (or both) surfaces may be bonded to a layer of textile or other ornamental material, which has the further advantage of making the visor stiffer. As herein described, a principal feature of the visor is that it is a commercially available type used for other purposes. Visor 11 has a central portion 12 or bill having a curved inner edge 13 and a curved outer edge 14, the latter being of a smaller radius of curvature than edge 13. Projecting from one side of central portion 12 is a left tail 16 which consists of a narrow band on which are mounted at spaced intervals snaps 17. The right tail 18 is similarly constructed and is provided with spaced snaps 19. Other fastening means may be used, as in FIGS. 6—8, for example. It will be understood that the shape and features of the visor may be widely varied within the spirit of the present invention. The commercially available visor is modified in accordance with the present invention by the provision of spaced slits 21 along the outer margin of the central portion 12 spaced slightly inward from the edge 14.

For surgical uses it is desirable that the visor 11 be capable of being sterilized. So that the device may be packaged in an aseptic manner, the visor 11 is preferably foldable. Because of the danger of cross-contamination of patients, it is likewise desirable that the entire visor and shield (hereinafter described) be of inexpensive construction so that they may be discarded after each use. However the components may be sterilized (as by use of ethylene dioxide gas or liquid disinfectants) after use.

It will be noted that one of the features of the invention is the fact that the central portion 12 is resilient (i.e., made of a rubber or rubber-like material), so that when the shield is attached by projection through the slits 21, the shield is adequately supported. The shield also helps rigidify the visor.

Shield 26 is preferably made of a clear plastic material. It has a curved upper edge 27 from which project dovetail projections 28 having truncated corners 29. The spacing of projections 28 complements the slits 21 and the dimensions of the projections 28 are such that they may be pushed through the slits 21, stretching the elastic material surrounding the slits which then resumes its initial shape so that the dovetail projections 28 may not escape therefrom until they are manually removed.

Although the shape of shield 26 is subject to some modification, it preferably covers the eyes, nose and mouth of the user so that in transverse horizontal section it is approximately semicircular. Thus the sides 31 converge, terminating in a bottom edge 32 which is at about the level of the chin of the user. Uncontaminated air enters behind the shield 26 and any breath expelled from the mouth is discharged to the atmosphere rather than being rebreathed. The present mask may be worn over an ordinary surgeon's mask, if desired.

FIG. 6 illustrates a modification wherein the snaps 17, 19 of FIGS. 1 and 1 are replaced by patches of felt-like material 36 and hook-containing material 37 suitably affixed to the ends of tails 16a and 18a respectively. Materials 36 and 37 are of the well-known Velcro type.

In FIG. 7, tail 18b is preferably enlarged at its end 41 and formed with spaced transverse slots 42. The rounded end 43 of tail 16b is inserted up through the outer slot 42 and down through the inner slot.

Buckle 48 of FIG. 8 has a transverse connection 47. The outer end 48 of the tail 18c is brought around connection 47 and secured overlapped. The end of tail 16c is brought through the buckle.

Various other ways adjust the tails to the size of the head of the user. In those shown in FIGS. 6, 7 and 8 the subscripts a, b and c respectively, are added to the numerals referenced in FIGS. 1–5 to designate corresponding parts.

When the tails are fastened together, the visor central portion 12 assumes an upward-convex shape shown in FIG. 1.

FIGS. 9 and 10 illustrate a second preferred embodiment. Visor 11d is stamped out of a flat piece of material with an ellipsoid hole 51 behind the central portion 12d. Thus there is a strap 52 which fits flat against the back of the head and sides 53 which fit along the sides of the head. Inner visor edge 13d is a portion of the edge of hole 51 and fits across the forehead. The central portion 12d is upward convex.

The material of construction of visor 11d may be the same as visor 11, cross-linked polyethylene being preferred. Neoprene and nylon covering are also suitable.

As shown in FIG. 11, in either of the versions of FIGS. 1-8 or FIGS. 9-10, the upper (or lower, or both) surfaces of the resilient material 56 may be surfaced with a fabric or non-woven material 57. This facilitates ornamentation of the visor and also tends to make it more rigid. It also prevents tearing as it limits the amount of expansion which it will undergo.

Shield 26 shown in FIG. 9 may be secured to visor 11d by slits 21d and projections 28, as in the preceding modification, or by other means as has been discussed. Many of the elements of the structure of FIGS. 9 and 10 resemble those of FIGS. 1 and 2 and the same reference numerals, followed by subscript d are used to designate corresponding parts.

In the embodiment of FIG. 12, tails 16e and 18e are shorter than in FIG. 1, extending about to the ears.

Holes are formed in two places near the end of each tail, one closer to edge 13e the other. Holes 62 are formed further toward the center of portion 11e than holes 61.

Each end of tube 63 of stretchable material such as surgical tubing passes through a hole 61 and a hole 62, choice of the holes governing how far from the forehead edge 14e extends and hence how far in front of the face shield 26 hangs. One way to secure tube 63 is to insert the end of the tube through a washer 66, having a hole slightly bigger than tube 63, then insert the tube through holes 61 and 62 and then insert a ball 67 in the end of the tube of a diameter greater than the inside diameter of the tube. The washer 66 slants at an angle to the tube 63 and thus engages the same. The ball 67 expands tube 63 and prevents the end of the tube from slipping out of holes 61 or 62.

What is claimed is:

1. A face mask comprising a visor initially formed of a flat sheet of material which is bendable, first means comprising a bill to be attached to the forehead projecting forwardly and second means for attaching the visor to the head of the wearer said second means comprising a first and a second narrow tail, said tails having cooperating fastening means to adjustably fit around the head, said visor being formed with first cooperating means along the outer edge of said visor and a shield of flexible transparent plastic, said shield being initially flat and having an upper edge formed with second cooperating means shaped and positioned to engage said cooperating means so that said shield is supported extending freely substantially vertically downward approximately perpendicular to said visor, said shield being dimensioned to extend down below the mouth and around the face, said first cooperating means comprising at least four spaced slits through the outer edge of said visor and said second cooperating means comprises projections dimensioned to be forced through each of said slits.

2. A mask according to claim 1 in which said first means further comprises first cooperating means on the rearward edges of said tails, a member formed of a length of stretchable material dimensioned to fit behind the head of the wearer and having second cooperating means on each end engageable with said first cooperating means.

3. A mask according to claim 2, in which said first cooperating means comprises plural holes in said tails and said second cooperating means secures said ends of said member in one of said holes.

4. A mask according to claim 1 in which said projections are dovetail, having a maximum width greater than the lengths of said slits when said visor is unstressed.

5. A mask according to claim 4 in which the outer corners of said projections are truncated.

6. A face mask comprising a visor initially formed of a flat sheet of material which is bendable, first means comprising a bill to be attached to the forehead projecting forwardly and second means for attaching the visor to the head of the wearer, said visor being formed with first cooperating means along the outer edge of said visor and a shield of flexible transparent plastic, said shield being initially flat and having an upper edge formed with second cooperating means shaped and positioned to engage said first cooperating means so that said shield is supported extending freely substantially vertically downward approximately perpendicular to said visor, said shield being dimensioned to extend down below the mouth and around the face, said first cooperating means comprising at least four spaced slits through the outer edge of said visor and said second cooperating means comprising projections dimensioned to be forced through said slits, said second means being formed by a hole in said visor, said visor being of a continuous piece of resilient material having an integral narrow band around one end of said hole adapted to fit around the back of the head of the wearer, said visor having a bill on the side of said hole opposite said band.

7. A mask according to claim 1 in which said fastening means are interfitting snaps.

8. A mask according to claim 1 in which said fastening means are Velcro-like materials.

9. A mask according to claim 1 in which said fastening means comprises a buckle in one said tail and means adapted to be engaged by said buckle in the other said tail.

* * * * *